United States Patent [19]

Hitzman

[11] Patent Number: 4,596,778

[45] Date of Patent: Jun. 24, 1986

[54] SINGLE CELL PROTEIN FROM SULFUR ENERGY SOURCES

[75] Inventor: Donald O. Hitzman, Bartlesville, Okla.

[73] Assignee: Phillips Petroleum Company, Bartlesville, Okla.

[21] Appl. No.: 511,127

[22] Filed: Jul. 6, 1983

[51] Int. Cl.$^4$ .............................................. C12N 1/20
[52] U.S. Cl. ..................... 435/253; 426/656; 435/68; 435/130; 435/804; 435/822; 435/938
[58] Field of Search ................ 435/68, 130, 262, 251, 435/253, 822, 804, 289, 3, 938; 426/7, 656; 47/1.4; 210/611

[56] References Cited

U.S. PATENT DOCUMENTS

| | | | |
|---|---|---|---|
| 2,521,761 | 9/1950 | Strawinski | 435/282 |
| 2,525,214 | 10/1950 | Ekelund | 435/164 |
| 2,574,070 | 11/1951 | Strawinski | 435/282 |
| 3,069,325 | 12/1962 | Hitzman | 435/248 |
| 3,105,014 | 9/1963 | Harrison | 166/246 |
| 3,607,235 | 9/1971 | Duncan et al. | 423/41 |
| 3,711,372 | 1/1973 | Donnelly | 435/128 |
| 3,711,392 | 1/1973 | Metzger | 204/180 R |
| 3,713,976 | 1/1973 | Bunting et al. | 435/248 |
| 3,714,063 | 1/1973 | Salomone | 252/312 |
| 3,844,893 | 10/1974 | Hitzman | 435/247 |
| 3,862,006 | 1/1975 | Abe et al. | 435/247 |
| 4,044,500 | 8/1977 | Hitzman | 47/1.4 |
| 4,124,501 | 11/1978 | Yen et al. | 435/262 |
| 4,200,523 | 4/1980 | Balmat | 210/611 |
| 4,414,329 | 11/1983 | Wegner | 435/68 |
| 4,426,450 | 1/1984 | Donofrio | 435/243 |

FOREIGN PATENT DOCUMENTS

| | | | |
|---|---|---|---|
| 1149298 | 7/1983 | Canada | 195/34.9 |

OTHER PUBLICATIONS

Bergey's Manual of Determinative Bacteriology, 8th Edition, 1974, pp. 456-457.
C & EN, Mar. 5, 1984, p. 19.
Macmillan Journals Ltd., 1984, Nature, vol. 307, 2-2-3-84, "Possible Artefactual Basis for Apparent Bacterial Growth at 250° C."–Trent et al.
Chem. Engr., Dec. 14, 1981, pp. 19-20.
C & EN, Sep. 22, 1980, p. 66.
C & EN, Mar. 10, 1980, pp. 30-33.
Scientific American, May, 1981, vol. 244, No. 5, pp. 100-116, Macdonald et al, "The Crest of the East Pacific Rise".
Sea Grant Today, Jul./Aug. 1980, vol. 10, No. 4, pp. 5-6, Gately, "Farming of the Future?".
Science News, Nov. 3, 1979, vol. 116, No. 18, p. 317, Miller, "Hot Bug for Energy".
Haggin, "Sulfide Ores May Ease Minerals Shortage", C & EN, Jan. 4, 1982, pp. 21-23.
C & EN, Feb. 8, 1982, p. 30.
C & EN, May 10, 1982, "Bacterium May Clean Industrial Gas Streams", pp. 48-49.
Jannasch, et al, "Deep-Sea Bacteria: Isolation in the Absence of Decompression", Science, vol. 216, (1982) pp. 1315-1317.

Primary Examiner—Christine M. Nucker
Assistant Examiner—William J. Herald
Attorney, Agent, or Firm—Lyell H. Carver

[57] ABSTRACT

Single cell protein is produced in an aqueous fermentation process employing an oxidizable sulfur energy source plus a carbon dioxide source, such as hydrogen sulfide and carbon dioxide, in a controlled oxygen aqueous environment. The process also can employ carbon dioxide containing off-gases from a conventional aqueous fermentation process employing a conventional oxidizable carbon energy source, such as methanol.

17 Claims, No Drawings

SINGLE CELL PROTEIN FROM SULFUR ENERGY SOURCES

FIELD OF THE INVENTION

The invention pertains to single cell protein. In one aspect, the invention pertains to the production of single cell protein employing a combination of an oxidizable-sulfur source as sulfur energy source can a carbon dioxide-containing source or carbon dioxide-precursor as carbon source. In another aspect, the invention pertains to a method to reduce the wastage of carbon substrate in a conventional aerobic aqueous fermentation process. In a further aspect, the invention pertains to the production of single cell protein of enhanced sulfur-containing amino acid balance. In a still further aspect, the invention pertains to a tandem single cell protein fermentation system for production of single cell protein with improved utilization of carbon energy substrate.

BACKGROUND OF THE INVENTION

Efforts to relieve world-wide shortages of protein have included various bio-synthesis processes in which single cell protein (SCP) is produced by the aerobic aqueous fermentation of one or another of a variety of fungi, yeasts, or bacteria on various carbon energy substrates.

Attention has centered on carbon energy substrates which are readily available, cheap, uniform, safe, and preferably relatively water-soluble, such as the lower saturated aliphatic alcohols, primarily of 1 to 4 carbon atoms, and most generally methanol and/or ethanol.

In conventional aerobic aqueous fermentation processes, a limiting cost factor has been the loss (wastage) of the carbon substrate to carbon dioxide. Varying amounts of substrate actually become incorporated into the cell structure, for example roughly somewhat less than about half of the methanol and about 50 to 75% of the ethanol. The remainder of the substrate is converted to carbon dioxide and wasted as an off-gas. Even though various methods have proposed recovery of the carbon dioxide by employment thereof such as in a water-gas reaction, or reaction with a reducing agent such as methane to form additional methanol, or reaction with ammonia to produce urea, such schemes have not been found commercially viable, at least as yet.

Another problem encountered in conventional aerobic aqueous fermentation processes using carbon energy substrates has been the persistently low sulfur amino acid content of the produced single cell protein. Such SCP frequently requires supplementation with synthetically produced sulfur containing amino acids.

I have discovered practical and effective solutions to these problems.

BRIEF DESCRIPTION OF THE INVENTION

I have discovered (A) that sulfur-oxidizing and metabolizing bacteria can be utilized in a controlled oxygen-limited aerobic high salts/high cell density aqueous fermentation process utilizing a combination substrate of an oxidizable sulfur-energy-source plus a carbon dioxide-carbon-source to produce a single cell protein (SCP) product. I have also discovered (B) a tandem fermentation process by which the sulfur oxidizing metabolizing fermentation employs the oxygen- and carbon dioxide-containing off-gases from an aerobic aqueous carbon substrate fermentation. Each fermentation step or stage in the tandem process can operate at high or low salts conditions, though high salts/high cell conditions are preferred for each. My tandem process effectively obtains greater economies of carbon and oxygen usage.

DETAILED DESCRIPTION OF THE INVENTION

(A) Sulfur-Oxidizing Fermentation

In one aspect, my invention provides an aqueous controlled oxygen fermentation employing a sulfur-oxidizing, metabolizing bacterium as the microorganism, as oxidizable sulfur energy source, a carbon dioxide carbon source, under high mineral salts/high cellular density fermentation conditions.

The aqueous sulfur-oxidizing fermentation process is conducted under what I term controlled oxygen-limiting conditions. The controlled oxygen-limiting method permits the sulfur-oxidizing microorganisms to utilize virtually all of the oxidizable sulfur-source, rather than tolerate undue loss by chemical oxidation of the sulfur-source to sulfate without utilization by the bacteria. Using $H_2S$ as typical and illustrative of oxidizable sulfur sources, the $H_2S:O_2$ balance requires some $O_2$ in the aqueous ferment all of the time. It is the solubilities of the $H_2S$ and of the $O_2$ which are critical. Too much $H_2S$ tends to result in too low an $O_2$ level; too much $O_2$ tends to eliminate the $H_2S$ by chemical oxidation. The feed of each must be balanced so that the metabolism of the microorganisms effectively dominates the undesirable (competing) chemical reaction such that the microorganisms are always supplied with both $O_2$ and $H_2S$, but not too much to too little of either.

A high bacterial population is achieved and maintained under the high salts/high cell density fermentation operation by the continuous or semi-continuous feed of necessary aqueous salts, pH control, substrates and other supportive requirements, and, after the appropriate cell density is built up, operating with continuous or substantially continuous withdrawal of aqueous ferment.

Under my high mineral salts/high bacterial cellular density operation, a bacterial cell density of 40 to 160, more usually 70 to 120, grams per liter is maintained. Cell density, usually expressed as grams/liter, is defined as the concentration of cells by weight on a dry basis per volume of ferment.

Sulfur-Oxidizing Metabolizing Microorganisms

The microorganisms employed are those broadly classed as the sulfur-oxidizing metabolizing class of bacteria. These bacteria utilize sulfur in a suitable metabolizable reduced form as an energy source, and thus the microorganisms derive their energy primarily from the oxidation of an oxidizable sulfur-containing source. Sulfate-reducing types of bacteria are not suitable.

Typical types of suitable sulfur-oxidizing bacteria include the family Thiobactericae, and of these such as the genus Thiobacillus. Bacteria of the family Sulfolobus also are suitable. Other suitable microorganisms include species of the genera Thiobacterium, Macromonas, Thiovulum, and Thiospira, as well as organisms obtained from deep sea vents, all of which utilize sulfur in a sulfur-oxidizing metabolism process.

Sulfur Substrate

Suitable sulfur-sources for the sulfur-oxidizing metabolizing microorganisms are the oxidizable sulfur sources.

Suitable oxidizable sulfur energy sources include elemental sulfur as such, either in a finely divided water-dispersible form or preferably in a water-wettable form, mercaptans and disulfides, the water-soluble sulfides, and presently preferred hydrogen sulfide for its wide-spread availability and relative cheapness, as well as such as the alkali metal and ammonium sulfides and hydrogen sulfides (bisulfides), and the alkali metal and ammonium thiosulfates, specifically those of potassium and sodium. Impure sulfur sources can be utilized, such as various sour-gas streams, gaseous streams from hydrogen sulfide-producing wells, and the like.

The process of energy usage by the microorganisms results in oxidation of the sulfur-substrate, such as sulfide to sulfur or sulfate, thiosulfate to sulfate, sulfur to sulfate, and the like, under controlled oxygen-limiting conditions.

The oxidizable sulfur-source should be fed to or maintained in the aqueous ferment in the amount required by, or which is that just needed for, the microorganisms to grow and metabolize. The feed rate with some low-solubility substrates depends on the solubility of the sulfur-source compound. Highly-soluble sulfur-source substrates should be fed depending on the "take-up rate" by the microorganisms, which varies depending on microorganism, relative population, growth phase whether exponential or otherwise, as can be readily determined by one skilled in the art. Wanted is enough, but not too much, since it is recognized that excess oxidizable-sulfur substrate may be inhibitory, or even toxic to the bacteria. The feed rate can be controlled by monitoring the off-gases from the fermentor, and feeding as much sulfur-source as is being taken up by the microorganisms, without wastage in the off-gases. The "take-up rate" should govern the feed control rate.

The oxidizable-sulfur source can be added directly to the aqueous ferment contained in the fermentor, or added diluted with or dissolved in or admixed with water.

Carbon Dioxide Source

The carbon source, also necessary for proper growth of the sulfur-oxidizing and metabolizing bacterial cells, is characterized as a carbon dioxide-source material.

The carbon dioxide-source can be any convenient carbon dioxide source, particularly $CO_2$ itself, such as from a $CO_2$ well, $CO_2$ separated from a methane/$CO_2$ producing well, $CO_2$ produced from carbon combustion processes such as separation from power plant stack gases, and the like.

Other carbon dioxide-source materials can be employed, such as the ammonium, sodium, or potassium bicarbonates or carbonates, which can be added, preferably predissolved in water, to the aqueous ferment for utilization by the oxidizable-sulfur utilizing-bacteria.

The amount of carbon dioxide-source to be employed relative to the oxidizable sulfur source preferably should be that amount required by, or that amount just needed for, the microorganisms to grow and metabolize. The amount needed is that amount which is just over the amount being taken up by maintenance of the microorganism population and the growth (reproduction) rates. The feed rate can be controlled by monitoring the off-gases from the fermentor, and controlling the feeding of the $CO_2$-source at a rate consistent with at least the take-up rate, feeding at least as much as is being taken-up (used) by the microorganisms, without undue wastage in the off-gases. Of course, with $CO_2$, an excess is not usually objectionable (contrary to the situation with the sulfur-source), merely representing a minor loss of otherwise utilizable material.

The $CO_2$-source can be added directly to the aqueous ferment either in a gaseous form, or dissolved in or admixed with water, as may be suitble and convenient.

Where suitable and convenient, the oxidizable sulfur-source and the $CO_2$-source can be fed together, such as a $CO_2$-containing stream admixed in desired proportions with a hydrogen sulfide-containing stream, before adding to the aqueous ferment, for feeding and control purposes.

Controlled Oxygen

The metabolism of the oxidizable sulfur metabolizing microorganisms employed in the aqueous fermentation process which oxidizes the sulfur to some higher oxidation stage, also utilizes the $CO_2$-source for the necessary body-building carbon, and does require oxygen. However, the metabolism does not employ the saturated excess molecular oxygen conditions in the aqueous ferment usually considered necessary in conventional aerobic aqueous fermentation processes utilizing an energy source an oxidizable carbon source such as a carbohydrate or methanol.

The microorganisms need molecular oxygen in their process of obtaining energy from their metabolism of an oxidizable-sulfur compound. But, the feed rate of oxygen should be sufficient for the use-demand (uptake rate) without a large excess. If a large excess of oxygen is fed into and through the aqueous ferment, competing chemical oxidation reactions tend to occur with loss of sulfur substrate without use thereof by the microorganisms.

My process preferably is operated so as to utilize about 80 to 90 mol percent of the applied sulfur-source and of the applied oxygen. Either of these constituents can be a limiting or controlling factor of the metabolic rate. The feed of each should be closely monitored, feeding slowly at first as the fermentation system begins after inoculation with the selected microorganism culture, monitoring the off-gases to watch take-up rates, and increasing feed of each as the bacterial population increases and consumes more sulfur-source and molecular oxygen.

Fermentation Conditions

My process of producing single cell protein (SCP) from an oxidizable sulfur-source is conducted at high salts/high cell densities. Heretofore, no one has utilized an oxidizable-sulfur-source employing sulfur-oxidizing bacteria at high cell density conditions.

The method achieves high levels of substrate utilization by adding media containing high mineral salts concentrations to the ferment in the fermentor. This enables high yields of single cell protein and high levels of extracellular product formation. Yield is defined as the amount of cells by weight produced for a given consumption by weight of carbon source or substrate fed to the ferment, and is usually expressed in grams/gram, grams of cells on a dry basis/gram of substrate.

In typical high salts/high cell density sulfur-oxidizing bacteria fermentations, once operating equilibrium and cell density equilibrium are attained, the ferment comprises about half supernatant medium and half cells, by volume. The one-half by volume cells, however, contain at least about two-thirds of the mineral salts content of the aqueous ferment. The aqueous ferment is defined as the total volume of aqueous fermentation broth or liquor, including cells.

Although the composition of the ferment can vary over a wide range, depending in part on the bacterium and substrate employed, the minerals content in the ferment (that is, liquid plus cells) is relatively high. Set forth in Table I below are the minimum, broad, and presently preferred ranges of concentrations of various elements in the ferment, the concentration being expressed as of the element, though it is recognized that all or part of each can be present in the form of a soluble ion, or in cases such as P which is present in a combined form such as the phosphate. The amount of each element is expressed in grams or milligrams per liter of ferment (aqueous phase, including cells):

TABLE I

| | Weight of Element per Liter of Ferment | | |
|---|---|---|---|
| Element | Minimum | Broad Range | Preferred Range |
| P | 1.9 g | 2.9–20 g | 2.2–10 g |
| K | 1 g | 1–20 g | 1.5–10 g |
| Mg | 0.5 g | 0.15–3 g | 0.3–1.2 g |
| Ca | 0.06 g | 0.06–1.6 g | 0.08–0.8 g |
| Fe | 6 mg | 6–140 mg | 9–80 mg |
| Zn | 2 mg | 2–100 mg | 3–40 mg |
| Cu | 0.6 mg | 0.6–16 mg | 1–10 mg |
| Mn | 0.6 mg | 0.6–10 mg | 0.9–8 mg |

Preferably, the magnesium, calcium, iron, zinc, copper, and manganese are employed in water-soluble form, such as the chloride. The potassium preferably is employed as a chloride or phosphate. The phosphorus preferably is employed in the form of phosphoric acid or in the form of a phosphate, monohydrogen phosphate, or dihydrogen phosphate, e.g., as a potassium or ammonium salt.

Conveniently, a primary mineral salts medium is employed to include nutrients comprising P, K, Mg, and Ca; and a trace mineral medium to supply nutrients comprising Fe, Zn, Mn, and Cu.

Other elements, which may be present at least in trace amounts, include such as sodium and cobalt, e.g., as a halide; molybdenum, e.g., as molybdate; boron, e.g., as borate; selenium, e.g., as selenite or selenate; and/or iodine, e.g., as iodide.

Vitamin additions usually are not needed in bacterial fermentations, but can be added.

The salts in the supernatant are at a relatively low concentration, since there is a high take-up by the growing reproducing bacterial cells. The mineral salts in the cells may not be present as fed or applied since some may be in a bound organic form. Mineral analysis of the aqueous ferment, of course, reflects a total mineral content.

With the utilization of thermally tolerant sulfur oxidizing bacteria, such as those discovered in and obtained from "deep sea vents" in recent years, fermentation in a sea water medium becomes practical, where desired. Thus in my inventive processes, sea water media can be employed. This can be very important in areas where fresh water is in short supply. The natural mineral content of sea water can be augmented with such other primary minerals and trace minerals as may be needed.

The assimilable nitrogen source can be any of the assimilable nitrogen sources generally utilizable in aqueous fermentation processes. Most useful are the ammonium compounds including ammonia itself, as well as such as ammonium carbonate, ammonium sulfate, ammonium chloride, ammonium nitrate, and the like. When necessary, ammonia can be utilized in part as pH control. When an ammonium sulfide or bisulfide is employed, such becomes a part of the sulfur source as well as part of the nitrogen-source, and the amounts of each such separate source can be reduced accordingly.

In an oxidizable-sulfur metabolizing system, the pH maintained in the aqueous ferment normally is in the range of about 1 to 8.5, preferably about 2 to 7, depending on the preference of the particular species and strain employed.

pH is controlled by such as ammonia addition, or the use of mineral acid such as dilute sulfuric acid, depending on the pH range needed. Most aqueous fermentations tend to be rather acidic, and generally an alkaline addition is needed periodically or continuously to control the pH.

In an oxidizable-sulfur metabolizing system, the temperature maintained in the aqueous ferment generally is in the range of about 10° C. to 100° C., generally about 15° C. to 60° C. However, the discovery of and utilization of thermophilic sulfur-oxidizing metabolizing microorganisms in producing single cell protein is important since such microorganisms tolerate relatively high aqueous temperatures up to such as about 50° C. to 100° C.+ and even higher, with high pressures such as in a range of about 0.1 to 100 atmospheres (10.13–10,132 kPa), more usually about 1 to 30 atmospheres (101.3–3,039 kPa), presently preferably about 1 to 5 atmospheres (101.3–506.5 kPa), as being suitable and convenient. High temperatures employable are substantially proportional to the pressure exerted and are operable up to the point where water is no longer liquid. The warmer the aqueous ferment that can be tolerated, the less cooling equipment is required and the less cooling that must be applied, and thus the more economical the reproductive process. Fermentations notoriously are producers of excess heat, which must be removed to properly control the production of desired microorganisms; thus, thermally tolerant bacteria are much to be preferred wherever utilizable.

Recovery

The average retention time of the aqueous ferment in the fermentor can vary considerably, depending in part on the fermentation temperature and culture employed. Generally, the retention time will be about 2 to 30 hours, presently preferably about 4 to 14 hours, based on average retention (the time which the average call spends in the fermentor).

The produced oxidizable-sulfur metabolizing microorganism cells (SCP) can be recovered from the aqueous ferment by means conventionally applied to the recovery of microbial cells. The cells can be separated from the aqueous liquor by such as centrifugation or filtering, before or after killing by such as heat, treatment with alcohol, or the like. Lysis can be used, though this is considered less preferred since initial recovery of whole bacterial cells usually is more convenient. The cells can be water-washed, as may be suitable or needed. Treatment steps can be applied to decrease the nucleic acid content of the cells, if desired, where the cells are to be utilized for human food rather than animal food purposes. Separated spent media can be recycled in order to re-use remaining minerals content. Or, separated media can be treated for recovery of various extra-cellular products such as enzymes.

(B) Tandem Process

As one aspect of my invention, I provide a tandem sequential two-step aqueous fermentation process. The first step is a continuous aqueous aerobic fermentation process utilizing an oxidizable-carbon energy substrate, molecular oxygen saturated conditions, assimilable nitrogen source, minerals, and an inoculum of a suitable SCP producing microorganism. The off-gases therefrom, comprising unconsumed molecular oxygen and importantly the heretofore-waste carbon dioxide, are used to furnish the carbon dioxide feed source to my paired second-in-sequence fermentation step. The second of my paired fermentation steps employs oxidizable sulfur-metabolizing microorganisms capable of utilizing the carbon dioxide and oxygen-containing off-gases to obtain the necessary carbon energy source as well as the modest oxygen requirements, supplemented by an oxidizable-sulfur energy source, as described above, conveniently such as hydrogen sulfide. This sequential tandem method substantially recovers the otherwise wasted carbon dioxide.

In my tandem process, the first stage is conducted under conventional aerobic (oxygen-saturation) aqueous fermentation conditions, employing an oxygenated hydrocarbon feedstock as oxidizable-carbon energy energy source. The term oxygenated hydrocarbon is intended to be a generic term in this disclosure descriptive of compounds employable, generally carbon-oxygen-hydrogen containing compounds (C-O-H compounds), and not a limiting term referring to the source of the substrate. The usable C-O-H compounds include such as the water-soluble carbohydrates, as well as those alcohols, ketones, esters, acids, and aldehydes, and mixtures, which are reasonably significantly water-soluble in character generally of 1 to 20 carbon atoms per molecule. The more suitable oxygenated hydrocarbons are those of substantially greater water-solubility of up to about 10 carbon atoms per molecule, or are the water-soluble carbohydrates generally.

Exemplary carbohydrates include glucose, fructose, galactose, lactose, sucrose, starch, dextrin, and the like, alone or in admixture. Of the other types of C-O-H compounds, those presently preferred are selected from linear alcohols of 1 to 4 carbon atoms, most preferably ethanol and/or methanol, though other materials of the described types are utilizable.

In the preferred tandem or dual process aspect of my invention, off-gases from the conventional aerobic aqueous fermentation process employing non-sulfur-utilizing bacteria, yeasts or fungi, which off-gases are predominantly unused or unconsumed oxygen plus by-product carbon dioxide, are utilized to supply the carbon dioxide and limited oxygen to the oxidizable sulfur metabolizing fermentation step of my tandem process. All that is needed to do is to augment the off-gases with the oxidizable sulfur source as feed to the successive oxidizable-sulfur fermentation step.

The particular microorganism strain employed, yeast, fungus, or bacterium, does not appear critical in the first stage of this aspect of my invention, so long as it is suitable for growth on the described oxygenated hydrocarbon feedstock under aqueous saturated oxygen conditions.

Fermentation Conditions

While any of the standard fermentation conditions for aerobic fermentation on an oxygenated hydrocarbon feedstock can be employed, the presently preferred condition is the high salts/high cell density process where high cellular and high mineral salts concentrations are maintained in the aqueous ferment.

According to my tandem process, the first stage employs a culture of a microorganism suitable for growth on carbon-containing substrates under saturated oxygen aerobic aqueous fermentation conditions. The microorganism can be chosen from yeasts, fungi, and bacteria.

Suitable yeasts include one or more species from the genera Candida, Hansenula, Torulopsis, Saccharomyces, Pichia, Debaryomyces, and Brettanomyces. The presently preferred genera include Candida, Hansenula, Torulopsis, Pichia, and Saccharomyces.

Presently preferred are the particular strains designated as, or which are derived from, the strains deposited as *Pichia pastoris* NRRL Y-11431, *Pichia pastoris* NRRL Y-11430, *Hansenula polymorpha* NRRL Y-11170, and *Hansenula polymorpha* NRRL Y-11432.

Among the suitable bacteria are the genera and their species Bacillus, Pseudomonas, Protaminobacter, Micrococcus, Arthobacter, Corynebacterium, Methanomonas, Methylococcus, Methylomonas, Methylobacter, Methylosinus, Methylocystis, Curtobacterium, Acinetobacter, Brevibacterium, Nocardia, Mycobacterium, Streptomyces, and Actinomyces.

Among presently preferred species are the thermophilic Bacillus species NRRL B-8065 and NRRL B-8066; and the mixed thermophilic culture NRRL B-8158.

Minerals, growth factors, vitamins, and the like, are added in amounts sufficient to provide for the particular needs of the particular microorganism utilized. Assimilable nitrogen compounds such as ammonia or an ammonium compound are added to the fermentation step. This first stage of my tandem fermentation process employs conditions generally known in the art to support aqueous aerobic fermentation.

Presently preferred is operation of the first stage under high salts/high cellular density conditions. The recommended mineral salts levels for high salts operation are as described hereinabove for the oxidizable-sulfur metabolizing aspect of my process (See Table I.). Sea water is useful and can be employed, augmented in minerals as needed, where the particular microorganism accepts such environment.

In addition to the mineral salts, when yeasts are employed, vitamins (organic growth factors) are normally employed in the ferment as is known in the art, when their presence is desirable for the propagation of the particular yeast chosen, such as one or both of the vitamins biotin and thiamine.

The first stage fermentation is an aerobic oxygen-saturated aqueous process. Molecular oxygen is supplied by air, oxygen-enriched air, or even substantially pure molecular oxygen, so as to maintain the ferment with an oxygen partial pressure effective to assist the microorganism species in growing or in biochemically converting oxidizable-carbon energy substrate in a thriving fashion. The rate at which molecular oxygen is supplied to the ferment should be such that the growth of the yeast or substrate conversion is not limited by lack of oxygen.

The pressure employed for the first stage microbial fermentation step can range widely. Typical pressures are about 0 to 150 psig, more usually about 35 to 40 psig. The fermentation temperature can vary somewhat, but generally is about 25° C. to 65° C., more usully about 28° C. to 50° C. Assimilable nitrogen is supplied by nitrogen-containing compounds, usually such as ammonia or ammonium hydroxide. Ammonia is convenient for large scale operations, and can be employed by bubbling through the aqueous microbial ferment in suitable amounts. At the same time, ammonia also assists in pH control.

The pH range in the first stage aqueous microbial ferment for yeasts should be in the range of about 3 to 7, more usually about 3.5 to 5.5; and for bacteria the pH should be in the range of about 4 to 9, more usually about 6 to 8. Preferences of certain microorganisms for a pH range are dependent to some extent on the medium employed, and thus may change somewhat with change in medium as can be readily determined by those skilled in the art.

The average retention time of the aqueous ferment in the fermentor can vary considerably, depending in part on the fermentation temperature and culture employed. Generally, the retention time will be about 2 to 30 hours, presently preferably about 4 to 14 hours, based on average retention.

High concentrations of some oxidizable-carbon C-O-H energy substrates, particularly such as methanol, may be inhibitory to satisfactory microbial growth or even toxic to the microorganisms in the fermentation. It is desirable to maintain the substrate concentration in the ferment at a maximum tolerable level. With the lower alcohols, this level in the ferment generally is about 0.001 to 5 volume percent, preferably about 0.005 to 0.05 volume percent, so as to neither starve nor inhibit the growth rates of the microorganisms chosen.

Conveniently, the fermentation is conducted in such a manner that the oxidizable C-O-H substrate is controlled as the limiting factor, thereby providing good conversion of the oxidizable carbon-containing substrate to cells and extracellular products. Continuous operation with continuous or semi-continuous feed of all components is much to be preferred for ease of control, production of uniform quantities of cells and extracellular products, and most economical uses of all equipment. The feed rates of the various material streams can be varied so as to obtain as rapid a cell growth rate as possible, consistent with efficient utilization of the oxidizable carbon energy source, to obtain as high a yield of bacterial or yeast cells and/or extracellular products, relative to substrate charge as possible, or to maximize the particular biochemical conversion being practiced. Yeast cells can be obtained, for example, in yields of about 30 to 110 grams per 100 grams substrate charged, depending in part on the particular substrate used.

In typical high cell density fermentation, the ferment comprises about one-half supernatant medium and one-half cells, by volume. The one-half by volume cells, however, contains at least about two-thirds of the mineral salts content of the ferment (liquid plus cells).

The microbial fermentation products from the first step aerobic aqueous fermentation step can be separately recovered by means known in the art such as centrifugation and/or filtration.

My tandem process produces both conventional single cell protein which normally is deficient in sulfur amino acid content, while the paired step utilizing the oxidizable-sulfur metabolizing bacteria produces single cell protein of enhanced sulfur amino acid content. The respective products can be utilized separately if desired, or more preferably can be admixed in suitable proportions to provide a more-balanced single cell protein product for animal feed purposes. Suitable treatment of the SCP for reduction of nucleic acid content can be employed to produce a product suitable for human consumption.

In my tandem process, in accordance with one aspect of my invention, the aqueous ferment from the oxidizable-sulfur metabolizing second step can be admixed with the aqueous ferment from the aerobic fermentation first step, in suitable proportion in accordance with the needs to produce a suitably amino acid balanced SCP product, and the entire admixture then subjected to recovery procedures. Where each step is conducted at a suitably high cellular density, in some cases, such as for animal food purposes, recovery can be direct drying of the aqueous ferments.

Separated aqueous liquors can be recycled to either fermentation step as may be convenient, or can be separately treated for recovery of extracellular biopolymers, and the like, as may be desired. Recycle of liquors, and of washings where washing of cells is employed, helps minimize waste disposal requirements.

EXAMPLES

Examples are provided to further exemplify my invention, as a part of my specification and disclosure. Particular materials employed, components, ingredients, species, and the like, should be considered exemplary and not limitative of the proper scope of my invention in its several aspects.

Example I

Several tubes of cultures of Thiobacillus species were obtained from the American Type Culture Collection in Rockville, Md. The cultures received were designated as follows:

|  | ATCC # |
| --- | --- |
| Thiobacillus thiooxidans | 8093 |
| Thiobacillus thioparus | 8158 |
| Thiobacillus intermedius | 15466 |
| Thiobacillus thiooxidans | 19377 |
| Thiobacillus concretivorus | 19703 |
| Thiobacillus neopolitanus | 23641 |
| Thiobacillus thermophilica imschenetsrii | 23841 |
| Thiobacillus sp. | 25364 |

The tubes of cultures received from the ATCC were opened, and the respective cultures grown on ATCC recommended media to provide sufficient culture for further manipulation. For example, ATCC #8148 was grown on Thiobacillus media $T_3$ (composition tabulated below), and ATCC #23841 was grown on Thiobacillus media $T_1$.

The nutrient media compositions prepared for use in studying the growth characteristics of the above mentioned Thiobacillus species are detailed in Table II:

TABLE II

Thiobacillus media $T_1$

TABLE II-continued

Thiobacillus media

| | |
|---|---|
| MgCl$_2$ | 0.1 g |
| NH$_4$Cl | 0.1 |
| Na$_2$HPO$_4$ | 0.2 |
| Na$_2$S$_2$O$_3$.5 H$_2$O | 5.0 |
| NaHCO$_3$ | 1.0 |
| H$_2$O, dist. | 1000 mL |
| | adjust pH to 7–7.2 |
| T$_2$ | |
| NH$_4$Cl | 0.3 g |
| KH$_2$PO$_4$ | 3.0 |
| CaCl$_2$.2 H$_2$O | 0.25 |
| MgSO$_4$.7 H$_2$O | 0.5 |
| FeSO$_4$.7 H$_2$O | 0.001 |
| elemental sublimed sulfur | 5 g |
| H$_2$O, deionized | 1000 mL |
| T$_3$ | |
| K$_2$HPO$_4$ | 2.0 g |
| CaCl$_2$.2 H$_2$O | 0.1 |
| MgSO$_4$.7 H$_2$O | 0.1 |
| FeSO$_4$.7 H$_2$O | trace |
| MnSO$_4$.H$_2$O | trace |
| H$_2$O, tap | 900 mL |
| | adjust pH to 7.8 |
| Na$_2$S$_2$O$_3$.5 H$_2$O | 10 g |
| H$_2$O, tap | 50 mL |
| (NH$_4$)$_2$SO$_4$ | 0.1 g |
| H$_2$O, tap | 50 mL |
| Total, | 1 L. |
| T$_4$ | |
| Na$_2$HPO$_4$ | 1.2 g |
| KH$_2$PO$_4$ | 1.8 |
| MgSO$_4$.7 H$_2$O | 0.1 |
| (NH$_4$)$_2$SO$_4$ | 0.1 |
| CaCl$_2$.2 H$_2$O | 0.03 |
| FeCl$_3$.6 H$_2$O | 0.02 |
| MnSO$_4$.H$_2$O | 0.02 |
| Na$_2$S$_2$O$_3$.5 H$_2$O | 10.0 |
| H$_2$O, deionized | 1000 mL |
| T$_5$ | |
| Na$_2$HPO$_4$ | 1.2 g |
| KH$_2$PO$_4$ | 1.8 |
| MgSO$_4$.7 H$_2$O | 0.1 |
| (NH$_4$)$_2$SO$_4$ | 0.1 |
| CaCl$_2$.2 H$_2$O | 0.03 |
| FeCl$_3$.6 H$_2$O | 0.02 |
| MnSO$_4$.H$_2$O | 0.02 |
| H$_2$S bubbled into solution | |
| H$_2$O deionized | 1000 mL |
| T$_7$ | |
| Na$_2$HPO$_4$ | 1.2 g |
| KH$_2$PO$_4$ | 1.8 |
| MgSO$_4$.7 H$_2$O | 0.1 |
| CaCl$_2$.2 H$_2$O | 0.03 |
| FeCl$_3$.6 H$_2$O | 0.02 |
| MnSO$_4$.H$_2$O | 0.02 |
| H$_2$O, deionized | 1000 mL |
| T$_8$ | |
| Na$_2$HPO$_4$ | 1.2 g |
| KH$_2$PO$_4$ | 1.8 |
| MgSO$_4$.7 H$_2$O | 0.1 |
| CaCl$_2$.2 H$_2$O | 0.03 |
| FeCl$_3$.6 H$_2$O | 0.02 |
| MnSO$_4$.H$_2$O | 0.02 |
| H$_2$O, deionized | 1000 mL |
| | adjust pH to 5.2 |
| T$_9$ | |
| Na$_2$HPO$_4$ | 1.2 g |
| KH$_2$PO$_4$ | 1.8 |
| MgSO$_4$.7 H$_2$O | 0.1 |
| CaCl$_2$.2 H$_2$O | 0.03 |
| FeCl$_3$.6 H$_2$O | 0.02 |
| MnSO$_4$.H$_2$O | 0.02 |
| (NH$_4$)$_2$SO$_4$ | 0.1 |
| H$_2$O, deionized | 1000 mL |
| T$_{10}$ | |
| Na$_2$HPO$_4$ | 1.2 g |
| KH$_2$PO$_4$ | 1.8 |
| MgSO$_4$.7 H$_2$O | .1 |
| CaCl$_2$.2 H$_2$O | .03 |
| FeCl$_3$.6 H$_2$O | .02 |
| MnSO$_4$.H$_2$O | .02 |
| (NH$_4$)$_2$SO$_4$ | .5 |
| Agar | 20 |
| H$_2$O, distilled | 1000 mL |
| | adjust pH to 4.2 |
| Nutrient Agar | |
| Bacto-Beef Extract | 3.0 g |
| Bacto Peptone | 5.0 |
| NaCl | 8.0 |
| Bacto-Agar | 15.0 |
| H$_2$O, distilled | 1000 mL |
| YM | |
| Yeast extract | 3.0 g |
| Malt extract | 3.0 |
| Peptone | 5.0 |
| Glucose | 10.0 |
| Agar | 20.0 |
| H$_2$O, distilled | 1000 mL |

Several of the Thiobacillus cultures were grown on various of the mineral media described above to study culture growth rates and responses to differing media. Results obtained, as shown below in Table III, were given comparative ratings:

| | | |
|---|---|---|
| − = | | No observable growth. |
| ± = | | Questionable growth. |
| + = | | Poor growth. |
| ++ = | ⎫ | |
| +++ = | ⎬ | Approximate qualitative comparisons. |
| ++++ = | ⎭ | |
| +++++ = | | Excellent growth. |

TABLE III

| Medium Designation | Sulfur Source, g | Nitrogen Source, g | Phosphorus Source, g | Magnesium Source, g | Calcium Source, g | Iron Source, g | Manganese Source, g | Misc. g |
|---|---|---|---|---|---|---|---|---|
| T$_1$ | Na$_2$S$_2$O$_3$.5 H$_2$O, 5.0 | NH$_4$Cl, 0.1 | Na$_2$HPO$_4$, 0.2 | MgCl$_2$.6 H$_2$O 0.1 | — | — | — | NaHCO$_3$, 1.0 |
| T$_2$ | Sublimed S, 5.0 | NH$_4$Cl, 0.3 | KH$_2$PO$_4$, 3.0 | MgSO$_4$.7 H$_2$O, 0.5 | CaCl$_2$.2 H$_2$O, 0.25 | FeSO$_4$.7 H$_2$O, 0.001 | — | — |
| T$_3$ | Na$_2$S$_2$O$_3$.5 H$_2$O, 10.0 | (NH$_4$)$_2$SO$_4$, 0.1 | KH$_2$PO$_4$, 2.0 | MgSO$_4$.7 H$_2$O, 0.1 | CaCl$_2$.2 H$_2$O, 0.1 | FeSO$_4$.7 H$_2$O, trace | MnSO$_4$.H$_2$O, trace | — |
| T$_4$ | Na$_2$S$_2$O$_3$.5 H$_2$O, 10.0 | (NH$_4$)$_2$SO$_4$, 0.1 | Na$_2$HPO$_4$/ KH$_2$PO$_4$, 1.2/1.8 | MgSO$_4$.7 H$_2$O, 0.1 | CaCl$_2$.2 H$_2$O, 0.03 | FeCl$_3$.6 H$_2$O, 0.02 | MnSO$_4$.H$_2$O, 0.02 | — |
| T$_5$ | H$_2$S (bubbled into solution) | (NH$_4$)$_2$SO$_4$, 0.1 | KH$_2$PO$_4$, 1.8 | MgSO$_4$.7 H$_2$O, 0.1 | CaCl$_2$.2 H$_2$O, 0.03 | FeCl$_3$.6 H$_2$O, 0.02 | MnSO$_4$.H$_2$O, 0.02 | — |
| T$_7$ | * | — | Na$_2$HPO$_4$/ KH$_2$PO$_4$, 1.2/1.8 | MgSO$_4$.7 H$_2$O, 0.1 | CaCl$_2$.2 H$_2$O, 0.03 | FeCl$_3$.6 H$_2$O, 0.02 | MnSO$_4$.H$_2$O, 0.02 | — |

TABLE III-continued

| Medium Designation | Sulfur Source, g | Nitrogen Source, g | Phosphorus Source, g | Magnesium Source, g | Calcium Source, g | Iron Source, g | Manganese Source, g | Misc. g |
|---|---|---|---|---|---|---|---|---|
| $T_8$ | * | — | $Na_2HPO_4/KH_2PO_4$, 1.2/1.8 | $MgSO_4.7 H_2O$, 0.1 | $CaCl_2.2 H_2O$, 0.03 | $FeCl_3.6 H_2O$, 0.02 | $MnSO_4.H_2O$, 0.02 | — |
| $T_9$ | * | $(NH_4)_2SO_4$, 0.1 | $Na_2HPO_4/KH_2PO_4$, 1.2/1.8 | $MgSO_4.7 H_2O$, 0.1 | $CaCl_2.2 H_2O$, 0.03 | $FeCl_3.6 H_2O$, 0.02 | $MnSO_4.H_2O$, 0.02 | — |
| $T_{10}$ | * | $(NH_4)_2SO_4$, 0.5 | $Na_2HPO_4/KH_2PO_4$, 1.2/1.8 | $MgSO_4.7 H_2O$, 0.1 | $CaCl_2.2 H_2O$, 0.03 | $FeCl_3.6 H_2O$, 0.02 | $MnSO_4.H_2O$, 0.02 | agar 20 |

*Various sulfur sources were employed with these media. Further formation is detailed below.

The growth of Thiobacillus thiooxidans ATCC 19377 was investigated on each of several mineral media. The results are tabulated below:

| Media | Relative Growth |
|---|---|
| $T_1$ | + |
| $T_2$ | — |
| $T_3$ | — |
| $T_4$ | — |

These results indicate that under the above conditions that *T. thiooxidans* ATCC 19377 grew poorly if at all on thiosulfate as energy source and does not utilize elemental sulfur as an energy source under the conditions employed.

The growth of *Thiobacillus thioparus* ATCC 8158 was investigated on several mineral media. The results are tabulated below:

| Media | Relative Growth |
|---|---|
| $T_1$ | — |
| $T_2$ | — |
| $T_3$ | ++ |
| $T_4$ | +++ |

These results indicate the *T. thioparus* ATCC 8158 grows well on thiosulfate as energy source with the appropriate mineral balance. In addition, elemental sulfur was not utilized as an energy source under the above conditions.

Example II

The growth of *T. thioparus* ATCC 8158 was further investigated on both streak plates and pour plates, employing a variety of mineral media as described above, as well as modifications thereof. The results are summarized in Table IV:

TABLE IV

| Growth Characteristics of *T. thioparus* ATCC 8158 | | |
|---|---|---|
| Medium | Method | Relative Growth |
| $T_4$ | pour | ++ |
| $T_4$ | streak | ++ |
| $T_5$ | pour | ++ |
| $T_5$ | streak | ++ |
| $T_5$ + [0.5 wt % $(NH_4)_2S$] | pour | +++ |
| $T_5$ + [0.5 wt % $(NH_4)_2S$] | streak | +++ |
| $T_4$ + [1 vol % methanol] | pour | ++++ |
| $T_4$ + [1 vol % methanol] | streak | +++++ |
| Nutrient agar | streak | — |

These results indicate that *T. thioparus* ATCC 8158 grows well on thiosulfate as energy source. This culture also utilizes sulfide as energy source and methanol as carbon source. These cultures differ little, if any, when grown on streak plates compared to pour plates, indicating they are facultative anaerobes.

Example III

The growth of *Thiobacillus novellus* ATCC 8093 was investigated on several mineral media. The results are tabulated below:

| Medium | Relative Growth |
|---|---|
| Nutrient agar | ++++ |
| $T_4$ | — |
| $T_4$ + vol % methanol | ± |
| $T_5$ | — |
| $T_5$ + 0.5 wt % $(NH_4)_2S$ | ++++ |

These results indicate that *T. novellus* ATCC 8093 utilizes sulfide as an energy source.

Example IV

The growth of *Thiobacillus thiooxidans* ATCC 19377 was investigated on several mineral media with added energy source. The results are tabulated below:

| Medium | Relative Growth |
|---|---|
| Nutrient agar | — |
| $T_4$ + 1 vol % methanol | — |
| $T_5$ + 0.5 wt % $(NH_4)_2S$ | +++ |

These results indicate that *T. thiooxidans* ATCC 19377 utilizes sulfide [in the form of $(NH_4)_2S$] as an energy source.

Example V

The growth of *Thiobacillus thermophilica imschenetsrii* ATCC 23841 was investigated on several mineral media. The results are tabulated below:

| Medium | Relative Growth |
|---|---|
| Nutrient agar | ± |
| $T_4$ | — |
| $T_4$ + 1 vol % methanol | — |

These results indicate that *T. thermophilica imschenetsrii* ATCC 23841 not utilize thiosulfate as an energy source uner the indicated conditions.

Example VI

Several sulfur-containing media were tested for their ability to support growth of Thiobacillus species. Results are summarized in Table V:

TABLE V
Relative Thiobacillus Growth on Various Sulfur-Containing Media

| | T. thiooxidans 19377 | T. thermophilica imschenetsrii 23841 |
|---|---|---|
| (a) Sodium sulfide containing: | | |
| $T_5$ + 0.5 wt % $Na_2S$ | +++ | +++ |
| $T_7$ + 0.5 wt % $Na_2S$ | ++ | ++ |
| $T_8$ + 0.5 wt % $Na_2S$ | + | + |
| (b) Ammonium sulfide containing: | | |

| | Thiobacillus | | | | | |
|---|---|---|---|---|---|---|
| | blank | novellus 8093 | thioparus 8158 | thiooxidans 19377 | neopolitanus 23641 | thermophilica imschenetsrii 23841 |
| $T_5$ + 0.5 wt % $(NH_4)_2S$ | − | + | ++ | ++ | ++ | ++ |
| $T_7$ + 0.5 wt % $(NH_4)_2S$ | − | ++ | ++ | ++ | ++ | ++ |
| $T_8$ + 0.5 wt % $(NH_4)_2S$ | − | ++ | ++ | ++ | ++ | ++ |
| (c) Thiosulfate containing: | | | | | | |
| $T_5$ + 0.5 wt % $Na_2S_2O_3$ | − | − | − | − | − | − |
| $T_7$ + 0.5 wt % $(NH_4)_2S_2O_3$ | | | | | − | − |
| $T_8$ + 0.5 wt % $(NH_4)_2S_2O_3$ | | | | | − | |

These results indicate that Thiobacillus species utilize sulfide as an energy source in a variety of nutrient medium compositions.

Example VII

Several Thiobacillus species were grown in flasks on a variety of sulfur containing media. The results are tabulated below in terms of relative growth in Table VI.

TABLE VI

| Medium | (b) 8093 | (c) 8158 | (d) 19377 | (e) 23641 | (f) 23841 |
|---|---|---|---|---|---|
| $T_4$ | + | + | − | − | ± |
| $T_8$ + 0.5 wt % $(NH_4)_2S$ | ± | ± | ± | ± | ± |
| $T_9$ + 0.5 vol % satd $Na_2S$ | + | + | + | + | ± |
| $T_8$ + [0.25 wt % $(NH_4)_2S$ + 0.25 vol % satd $Na_2S$] | ± | ± | ± | ± | ± |
| $T_8$ + [0.25 wt % $(NH_4)_2S$ + 1 vol % satd $Na_2S]^{(a)}$ | ± | ± | + | ± | ± |
| $T_8$ + [0.25 wt % $(NH_4)_2S$ + 0.5 vol % satd $Na_2S]^{(a)}$ | ± | ± | ± | ± | ± |
| $T_9$ + 1 vol % satd $Na_2S^{(a)}$ | ± | − | ± | − | ± |
| $T_8$ + [0.25 wt % $(NH_4)_2S$ + 0.5 vol % satd $Na_2S$] | − | + | + | + | − |
| Nutrient agar | − | − | − | − | − |

$^{(a)}$Grown on plates (specified medium + 20 g agar/liter).
$^{(b)}$Thiobacillus novellus.
$^{(c)}$Thiobacillus thioparus.
$^{(d)}$Thiobacillus thiooxidans.
$^{(e)}$Thiobacillus neopolitanus.
$^{(f)}$Thiobacillus thermophilica imschenetsrii.

This example indicates that Thiobacillus utilizes a variety of sulfur containing compounds as energy source including mixtures thereof.

Example VIII

Several Thiobacillus cultures were grown in $T_9$ medium with a range of sulfide content. The media adjustments employed are listed in Table VII:

TABLE VII

| Culture | Medium | | | |
|---|---|---|---|---|
| | A | B | C | D |
| T. novellus 8093 | ++ | +++ | − | − |
| T. thioparus 8158 | ++ | +++ | − | − |
| T. thiooxidans 19377 | ++ | +++ | − | − |
| T. neopolitanus 23641 | ++ | +++ | − | − |
| T. thermophilica imschenetsrii 23841 | ++ | +++ | − | − |

A - 0.5 vol % satd $Na_2S$
B - 0.1 vol % satd $(NH_4)_2S$ + 0.5 vol % satd $Na_2S$
C - 0.1 vol % satd $(NH_4)_2S$ + 1 vol % satd $Na_2S$
D - 0.1 vol % satd. $(NH_4)_2S$ + 0.5 vol % satd $Na_2S$ + $CO_2$ (from dry ice).

These results indicate that these organisms did not utilize $CO_2$ as carbon source under the prescribed conditions. It is clearly demonstrated that the media concentration of sulfur (energy) source is an important variable in the growth of Thiobacillus species.

Example IX

Cultures from the previous example which had grown very well on the nutrient medium [$T_9$+0.1 vol % satd $(NH_4)_2S$+0.5 vol % satd $Na_2S$] were cross-fed on several media. The media employed and results obtained were:

TABLE VIII

| Culture | Medium | | |
|---|---|---|---|
| | A | B | C |
| T. novellus 8093 | − | − | + |
| T. thioparus 8158 | − | − | +++ |
| T. thiooxidans 19377 | − | − | +++ |
| T. neopolitanus 23641 | + | − | +++ |
| T. thermophilica imschenetsrii 23841 | + | − | +++ |

A - $T_4$
B - YM
C - $T_9$ + 0.1 vol % satd $(NH_4)_2S$ + 0.5 vol % satd $Na_2S$ These results indicate that some of the Thiobacillus species which utilize sulfide as energy source also utilize thiosulfate as energy source.

Example X

Several modified nutrient media compositions were prepaed as follows:
A: $T_{10}$+0.5 vol % satd $Na_2S$ B: $T_{10}$+0.05 wt % yeast extract+0.5 vol % satd $Na_2S$ C: $T_{10}$+0.5 wt % $Na_2S_2O_3.5H_2O$ D: $T_{10}$+0.05 wt % yeast extract+0.5 wt % $Na_2S_2O_3.5H_2O$ Several Thiobacillus cultures were streaked on plates containing these media and growth response monitored.

| Culture | Medium | | | |
|---|---|---|---|---|
| | A | B | C | D |
| T. novellus 8093 | − | ± | − | − |
| T. thiooxidans 19377 | − | ± | ± | − |
| T. neopolitanus 23641 | ++ | +++ | ++ | ++++ |

These results indicate that *Thiobacillus neopolitanus* ATCC 23641 grows well on both sulfide and thiosulfate as energy source. Other Thiobacillus species such as *T. novellus* ATCC 8093 and *T. thiooxidans* ATCC 19377 grew poorly on a low ammonium medium such as formulation $T_{10}$.

The disclosure, including data, has illustrated the value and effectiveness of my invention. The examples, the knowledge and background of the field of the invention and the general principles of biochemistry, microbiology, and of other applicable sciences have formed the bases from which the broad descriptions of my invention including the ranges of conditions and the generic groups of operant components have been developed, and formed the bases for my claims here appended.

I claim:

1. A process which comprises culturing an oxidizing bacterium, employing an oxidizable sulfur source, a carbon dioxide carbon source, limited-molecular oxygen conditions, mineral medium, and water, as aqueous ferment, under high salts/high cell density conditions;

wherein said limited molecular oxygen conditions provide sufficient molecular oxygen for uptake rate needs of said microbial cells without oxidation of sulfur source by said molecular oxygen, and wherein in said high salts conditions sufficient minerals are employed to maintain in the aqueous ferment at least P 1.9 g. K 1 g, Mg 0.15 g, Ca 0.06 g, Fe 6 mg, Zn 2 mg, Cu 0.6 mg, and Mn 0.6 mg, per liter of aqueous ferment;

wherein in said high cell density conditions sufficient bacterial cell density is employed to maintain about 40 to about 160 grams of cells by weight on a dry basis per liter of ferment; and recovering the resulting microbial bacterial cells as a single cell protein food product.

2. The process according to claim 1 wherein said bacterium is selected from the group consisting of the genera Thiobacillus, Sulfolobus, Thiobacterium, Macromonas, Thiovulum, and Thiospira.

3. The process of claim 2 employing a species selected from the group consisting of:
   *Thiobacillus thiooxidans,*
   *Thiobacillus thioparus,*
   *Thiobacillus intermedius,*
   *Thiobacillus concretivorus,*
   Thiobacillus neopolitanus, and
   *Thiobacillus thermophilica imschenetsrii.*

4. The process of claim 3 wherein said oxidizable sulfur-source is a sulfide.

5. The process of claim 4 wherein said oxidizable sulfur-source is a hydrogen sulfide, and wherein the carbon dioxide-source is carbon dioxide.

6. The process of claim 5 wherein said water in said aqueous fermentation comprises sea water.

7. The sulfur amino acid enhanced single cell protein food made by the process of claim 1.

8. The process of claim 1 employing at least one microorganism obtained from deep sea vents capable of utilizing sulfur in a sulfur-oxidizing metabolism process.

9. A process with comprises:
   (a) culturing a yeast or bacterium, in aqueous ferment under aerobic fermentation conditions, employing molecular oxygen, assimilable nitrogen compound, oxidizable carbon-energy source, aqueous mineral medium, thereby producing microbial cells deficient in sulfur-amino acid content, and an off-gas comprising carbon dioxide and unconsumed oxygen;
   (b) cultivating at least one oxidizing bacterium under high salts/high cell density aqueous fermentation conditions employing an oxidizable-sulfur compound, aqueous mineral salts medium, assimilable nitrogen source, limited molecular oxygen conditions, and carbon dioxide-carbond source, thereby producing microbial bacterial cells of enhanced sulfur-amino acid content;
   wherein said limited molecular oxygen conditions provide sufficient molecular oxygen for uptake rate needs of said microbial cells without oxidation of sulfur source by said molecular oxygen,
   employing in said step (b) minerals sufficient to maintain in the aqueous ferment at least P 1.9 g, K 1 g, Mg 0.15 g, Ca 0.06 g, Fe 6 mg, Zn 2 mg, Cu 0.6 mg, and Mn 0.6 mg, per liter of aqueous ferment and a high cell density of about 40 to 160 grams of cells by weight on a dry basis per liter of ferment;
   (c) feeding said off-gas from said step (a) to said step (b) as at least a part of the molecular oxygen and carbon dioxide requirements therein; and
   (d) recovering said first and second microbial cells from each of steps (a) and (b) as a combined product.

10. The process of claim 9 employing in said step (b) a bacterium selected from the genera Thiobacillus, Sulfolobus, Thiobacterium, Macromonas, Thiovulum, and Thiospira, and microorganisms obtained from deep sea vents capable of utilizing sulfur in a sulfur-oxidizing metabolism process.

11. The process of claim 10 wherein said oxidizable sulfur-source is a sulfide.

12. The process of claim 11 wherein said oxidizable sulfur-source is hydrogen sulfide, and wherein the carbon dioxide-source is carbon dioxide.

13. The process of claim 9 employing sea water in at least one of said steps (a) and (b) to furnish at least a portion of the water and minerals therein.

14. The combined microbial cells product of claim 9.

15. The process of claim 9 employing in said step (b) at least one microorganism.

16. The process of claim 9 employing a yeast in said step (a).

17. The process of claim 16 wherein said yeast is a *Pichia pastoris.*

* * * * *

UNITED STATES PATENT AND TRADEMARK OFFICE
CERTIFICATE OF CORRECTION

PATENT NO. : 4,596,778
DATED : June 24, 1986
INVENTOR(S) : Donald O. Hitzman

It is certified that error appears in the above-identified patent and that said Letters Patent is hereby corrected as shown below:

Column 18, lines 61 and 62, delete claim 15.

Signed and Sealed this

Nineteenth Day of July, 1988

Attest:

DONALD J. QUIGG

Attesting Officer

Commissioner of Patents and Trademarks